United States Patent
Mehta (10) Patent No.: US 9,950,147 B2
(45) Date of Patent: Apr. 24, 2018

(54) APPARATUS AND METHOD FOR ADMINISTERING A SKIN CARE COMPOSITION

(71) Applicant: Je Matadi, Inc., Stafford, TX (US)

(72) Inventor: Pershant Mehta, Stafford, TX (US)

(73) Assignee: Je Matadi, Inc., Stafford, TX (US)

( * ) Notice: Subject to any disclaimer, the term of this patent is extended or adjusted under 35 U.S.C. 154(b) by 895 days.

(21) Appl. No.: 14/485,599

(22) Filed: Sep. 12, 2014

(65) Prior Publication Data

US 2016/0074641 A1   Mar. 17, 2016

(51) Int. Cl.
| A61H 1/00 | (2006.01) |
|---|---|
| A61M 35/00 | (2006.01) |
| A61H 7/00 | (2006.01) |
| A61H 9/00 | (2006.01) |
| A61H 23/02 | (2006.01) |

(52) U.S. Cl.
CPC .......... *A61M 35/003* (2013.01); *A61H 7/005* (2013.01); *A61H 9/0057* (2013.01); *A61H 23/02* (2013.01); *A61H 23/0263* (2013.01); *A61H 2201/0153* (2013.01); *A61H 2201/0207* (2013.01); *A61H 2201/1685* (2013.01)

(58) Field of Classification Search
CPC .... A61H 2201/0153; A61H 2201/0207; A61H 2201/1685; A61H 23/02; A61H 23/0263; A61H 7/005; A61H 9/0057; A61M 35/00; A61M 35/003
USPC ......................................... 601/46–55, 61–83
See application file for complete search history.

(56) References Cited

U.S. PATENT DOCUMENTS

| 5,003,966 A | 4/1991 | Saka et al. |
| 5,336,158 A * | 8/1994 | Huggins ................ A61H 9/005 601/14 |
| 6,023,639 A | 2/2000 | Hakty et al. |
| 6,319,211 B1 | 11/2001 | Ito et al. |
| 6,687,537 B2 * | 2/2004 | Bernabei ................ A61H 7/008 601/15 |
| 7,258,675 B2 | 8/2007 | Nichols |
| 7,399,297 B2 | 7/2008 | Ikadai et al. |
| 7,520,875 B2 * | 4/2009 | Bernabei ................ A61H 7/008 604/20 |
| 8,343,116 B2 * | 1/2013 | Ignon .................. A61M 35/003 604/289 |
| 2004/0073144 A1 | 4/2004 | Carava |

(Continued)

*Primary Examiner* — Susan Su (74) *Attorney, Agent, or Firm* — Andrew W. Chu; Craft Chu PLLC (57) ABSTRACT

The apparatus to administer a skin care composition includes a housing, a suction tip to engage the skin, a control module, a suction pump connected to a motor, a vibrator, and a power supply. The suction tip is placed on the skin with the skin care composition. The suction pump is activated to form an area of negative pressure. The vibrator generates vibrations to the area of negative pressure to further increase absorption of the skin care composition into the skin. The method of administering with the apparatus includes forming the area of negative pressure with the suction tip, and pulsing suction and suction with vibration. The control module regulates suction and vibration to maintain the area of negative pressure through personalized settings of intensity. The vibration is controlled to maintain the seal of the suction tip on the surface of skin.

18 Claims, 4 Drawing Sheets

(56) References Cited

U.S. PATENT DOCUMENTS

| | | | |
|---|---|---|---|
| 2005/0148910 A1* | 7/2005 | Skover | A61B 17/54 |
| | | | 601/46 |
| 2005/0159684 A1* | 7/2005 | Ikadai | A61M 1/0058 |
| | | | 601/6 |
| 2008/0065176 A1 | 3/2008 | Zhang et al. | |
| 2008/0091179 A1 | 4/2008 | Durkin et al. | |
| 2010/0049177 A1* | 2/2010 | Boone, III | A61H 9/0057 |
| | | | 606/9 |
| 2010/0056982 A1* | 3/2010 | Curaudeau | A61K 31/07 |
| | | | 604/20 |
| 2011/0089773 A1* | 4/2011 | Choi | G06F 3/016 |
| | | | 310/25 |
| 2011/0106067 A1 | 5/2011 | Geva et al. | |
| 2013/0116503 A1* | 5/2013 | Mertens | A61H 19/34 |
| | | | 600/38 |
| 2015/0182415 A1* | 7/2015 | Olkowski | A61H 23/02 |
| | | | 601/93 |
| 2017/0027809 A1* | 2/2017 | Lenke | A61H 19/30 |

* cited by examiner

APPARATUS AND METHOD FOR ADMINISTERING A SKIN CARE COMPOSITION

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to cosmetics. More particularly, the present invention relates to tools for administering skin care compositions. The present invention also relates to affecting absorption of the skin care composition.

2. Description of Related Art Including Information Disclosed Under 37 CFR 1.97 and 37 CFR 1.98

Skin care products are applied directly to the skin surface for absorption. The rate and efficiency of absorption is usually determined by the characteristics of the chemical composition and the biological features of the skin. There is tremendous variability. The chemical compositions can have components that evaporate quickly so that fast absorption is necessary to be effective. Other components may require more mechanical manipulation and time for absorption. Each individual may also have different skin, compared to another individual. Even different areas of the body of a single individual will have different skin types with different abilities to absorb skin care treatments. For example, working lotion into tough skin on the heel will differ from applying lotion to the face.

The prior art seeks to increase the absorption of skin care products by the skin, without regard to the characteristics of the chemical composition and the biological features. Other application factors can affect the rate of absorption so that the rate of absorption increases for any type of skin and any type of composition. A baseline rate of absorption for tough heel skin can be increased, as well as the baseline rate of absorption for sensitive facial skin. The baseline rate of absorption for a quick evaporating composition can be increased, as well as the baseline rate of absorption for a slow evaporating composition.

In particular, suction has been used to create a vacuum on the surface of the skin, any skin, to facilitate absorption. The suction causes a rush of blood and lymph to the skin from deeper tissues and opens blood vessels near the surface. The skin becomes more receptive to absorb the skin care product than the baseline rate of just applying the skin care product on the skin. No matter the composition or type of skin, there is an increase over the previous rate of absorption without suction.

In the past, various patents have issued in the field of suction and massage devices for the skin. U.S. Pat. No. 5,003,966, issued to Saka et al. on Apr. 2, 1991, describes a system and method for massaging skin by way of a suction force applied through a suction nozzle. The device generates suction through a diaphragm attached to a motor. The motor engages a dome shaped portion of the diaphragm which contracts and expands. An associated exhaust valve works with the suction valve to create a suction force against the skin.

U.S. Pat. No. 7,258,675, issued to Nichols on Aug. 21, 2007, describes a system and method for a facial rejuvenation device with a suction bore to provide a suction force to skin previously treated with a medicine or another formulation. The system includes a suction bore with an adjustable throttle. The throttle function is applied by adjusting the diameter of the suction bore inside the housing of the device. Depending on the direction the throttle knob is rotated by a user, a plunger moves in or out of the suction bore. The throttle controls speed and pulsing.

U.S. Pat. No. 7,399,297, issued to Ikadai et al. on Jul. 15, 2008, describes a system and method for a skin care device utilizing a suction pump for removing impurities from a user's skin. The preferred embodiment is comprised of a suction pump, a mist nozzle, a liquid storage tank, a liquid supply pump, and a drive motor. The drive motor and suction pump are used to create a suction force when the device contacts a user's skin. The mist nozzle is placed near the suction nozzle. By way of the liquid storage tank and liquid supply pump, it is used for spraying liquid on the user's skin. The motors, pumps, and tank are housed in the handle of the device. Although disclosed as a cleanser, the misting composition is analogous to skin treatment.

The use of suction in a handheld device is generally disclosed in the prior art. Various attachments, controls and settings can set the rate and intensity of the suction force. U.S. Pat. No. 6,319,211, issued to Ito et al. on Nov. 20, 2001, describes another cleanser system by use of suction. United States Patent Publication No. 20110106067, published for Geva et al. on May 5, 2011, discloses an advanced hand-held skincare system comprised of a handle and a number of different attachable heads. The device includes a small screen to display messages, including the status of the treatment, instructions, duration, and other messages. United States Patent Publication No. 20040073144, published for Carava on Apr. 15, 2004, describes another handheld negative pressure device for skin care.

It is an object of the present invention to provide an apparatus and method for administering a skin care composition.

It is an object of the present invention to provide an apparatus and method for administering a skin care composition with a suction force on the skin.

It is an object of the present invention to provide an apparatus and method for administering a skin care composition with an area of negative pressure on the skin.

It is another object of the present invention to provide an apparatus and method for administering a skin care composition with a suction force and vibration force.

It is an object of the present invention to provide an apparatus and method for administering a skin care composition with an area of negative pressure on the skin and mechanical vibration the area of negative pressure on the skin.

It is another object of the present invention to provide an apparatus and method for administering a skin care composition with a vibration force, during an application of a suction force.

It is still another object of the present invention to provide an apparatus and method for administering a skin care composition with a suction force maintained concurrent with a vibration force.

It is an object of the present invention to provide an apparatus and method for administering a skin care composition with an improved rate of absorption.

It is an object of the present invention to provide an apparatus and method for administering a skin care composition with an improved rate of breakdown of the skin care composition.

It is an object of the present invention to provide an apparatus and method for administering a skin care composition tailored for preferences of an individual user.

These and other objects and advantages of the present invention will become apparent from a reading of the attached specification and claims.

SUMMARY OF THE INVENTION

Embodiments of the apparatus to administer a skin care composition include a housing, a suction tip, a control module, a suction pump connected to a motor, a vibrator, and a power supply. The housing has a front side and a back side and is comprised of a handle portion and a head portion. The head portion sits on top of the handle portion and has a front end and a back end. The front end faces the front side of the housing, and the back end faces the back side of the housing. The handle portion can have a grip on the back side for the user to hold the apparatus.

The present invention includes the suction tip placed on the front end of the head portion so as to face the front side of the housing. The suction tip can form an area of negative pressure against the skin of the user. The suction tip is formed of a material suitable for contacting skin and sealing against skin and a skin care composition. The suction tip has variable shape and dimensions to seal against skin of different areas of the body. Additionally, the suction tip can have different sizes to adapt to skin of different areas of the body. The suction tip can have a generally concave surface, which deforms to form the area of negative pressure on the skin. The control module placed on the back end of the head portion connects to the motor and suction pump. An interface on the control module aligns with the handle portion and faces the back side of the housing so that the user can regulate the activity and intensity of the suction pump. There is also the vibrator in communication with the control module. The vibrator is mounted in the head portion and generates vibrations to the suction tip. The power supply is at least partially housed in the handle portion and connected to the control module, the motor, and the vibrator. A sealing cap at an end of the handle portion can enclose all components within the housing for a smooth and integrated aesthetic appearance.

In some embodiments of the present invention, the suction tip comprises a suction cup, having a concave surface facing outward to the front end of the head portion, an outer wall in fixed engagement to the front end of the head portion, and a ridge at a connection between the suction cup and the outer wall. In other embodiments, the suction tip comprises a suction chamber having a generally concave surface, an outer wall, and a cover piece facing outward to the front end of the head portion. The cover piece can have the ridge to form the area of negative pressure. The cover piece can also have protrusions to form secondary suction chambers so that the area of negative pressure is formed by the ridge and the secondary suction chambers in fluid connection.

Also, the suction tip can have a tubular receptacle behind the suction cup or suction chamber. The suction tip is removable from the housing, so that suction tips can be replaced after wear. The ridge or secondary suction chambers must be able to form a sealing engagement to skin and composition to affect administering the skin care composition to the skin. When the suction pump comprises a suction outlet extending outward toward the suction tip, the piston can be inserted into the tubular receptacle of suction tip. The suction force through the suction outlet deforms the suction tip to form the area of negative pressure.

The present invention includes the vibrator to add vibrations to the suction of the suction pump. The vibrator can be comprised of a magnet, a vibration motor, a weight, and a brush and commutator assembly. Movement of the weight within the head portion forms the vibrations. The area of negative pressure experiences the vibrations to further increase absorption of the skin care composition. The vacuum application is further enhanced by a particular mechanical manipulation of the skin applied at a specific time relative to the formation of the area of negative pressure. The area of negative pressure is formed by the suction tip before vibrations from the vibrator, and the suction tip maintains the area of negative pressure concurrent with vibrations from the vibrator. In another embodiment, there can be a heating element, such as a laser, to warm the area of negative pressure in coordination with the suction and vibration and suction.

Embodiments of the method to administer a skin care composition with the apparatus includes applying a skin care composition on a surface of skin, forming a seal with the suction tip around the surface of skin, forming an area of negative pressure on the surface of skin by activating the suction pump, and vibrating the area of negative pressure. The skin care composition may be absorbed through the surface of skin at a rate higher than regular suction and regular mechanical massage. The skin care composition may be broken down faster with the negative air pressure and mechanical vibration. The administration of the skin care composition to the skin is affected by the present invention. The vibration is stopped, and the area of negative pressure is released. The steps are repeated to pulse the surface of skin with suction, suction and vibration, and suction. The amounts and intensity are regulated by the control module according to individual preferences.

Further steps of embodiments of the method include releasing the seal with the suction tip, and removing the suction tip from the surface of skin. Excess skin care composition can be removed from the surface of skin. The vibration is concurrent with the suction, and the vibration can be coordinated at a predetermined amount of suction. Areas of various negative pressures can be maintained, and then the vibrator is activated to further increase uptake of the skin care composition. Once the amount of suction is set, the amount of vibration can be applied so as to maintain the suction and to administer the skin care composition. The amount of suction and vibration can be set by the individual user, but the amount of vibration remains regulated relative to the amount of suction in the present invention, so that area of negative pressure is maintained.

DETAILED DESCRIPTION OF THE DRAWINGS

Referring to FIGS. 1-8B, the apparatus 10 to administer a skin care composition is a handheld device for an individual user. The apparatus 10 is lightweight to be easily lifted and positioned on any area of the body. The compact and modular appearance facilitates storage and display of the apparatus 10. The individual user is apt to incorporate the apparatus 10 into a daily routine for skin care compositions. The rate of absorption of any skin care composition can be increased for skin on any area of the body. The breakdown of the skin care composition can be improved for any skin care composition. The apparatus 10 uses suction and vibration to affect the rate of absorption in a coordinated manner beyond prior art massagers and vacuum devices.

Embodiments of the apparatus 10, according the present invention include a housing 20, a suction tip 30, a control module 40, a motor 42, a suction pump 44, a vibrator 50, and a power supply 46. The control module 40 regulates the suction force by the suction tip 30 by the suction pump 44 and the vibration force by the vibrator 50.

Figure 1:
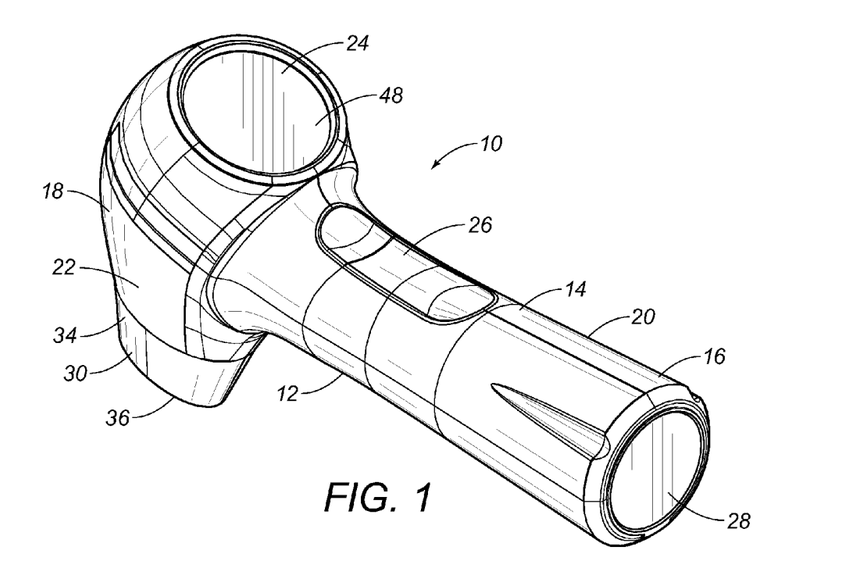
FIG. 1 is an upper perspective view an embodiment of the present invention, showing the apparatus to administer a skin care composition. The apparatus is a handheld device for an individual user.
Figure 2:
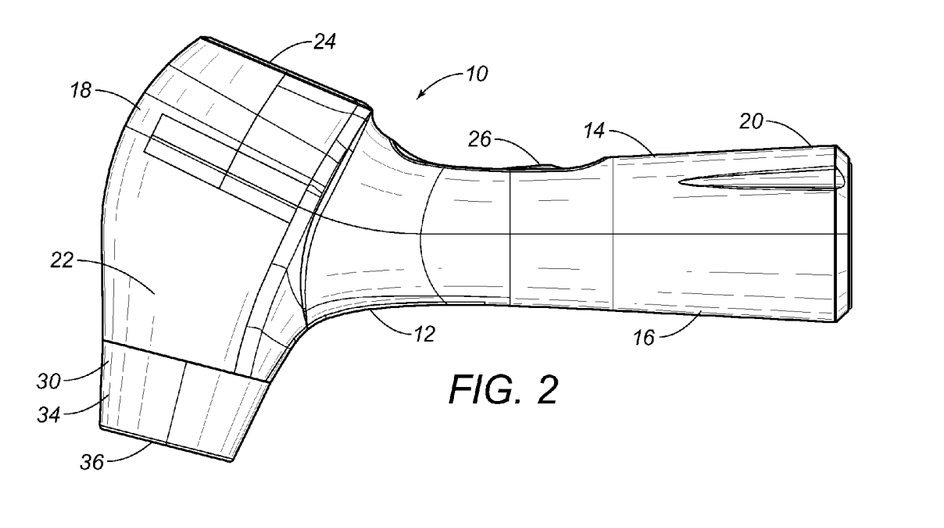
FIG. 2 is a side elevation view of an embodiment of the present invention, showing contours of the apparatus from the side.
Figure 3:
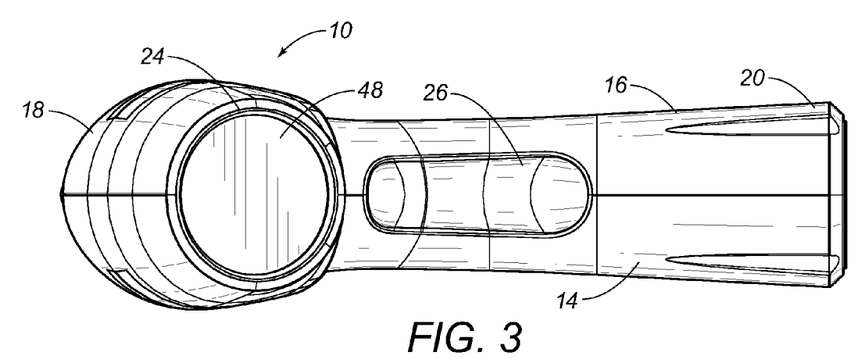
FIG. 3 is a back elevation view of the embodiment of the present invention from FIG. 1, showing the back side of the housing.
Figure 4:
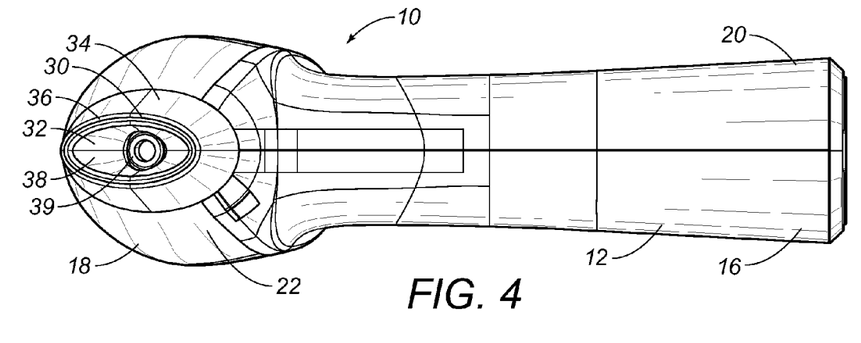
FIG. 4 is a front elevation view of the embodiment of the present invention from FIG. 1, showing the front side of the housing and the suction tip on the head portion of the housing.
Figure 5:
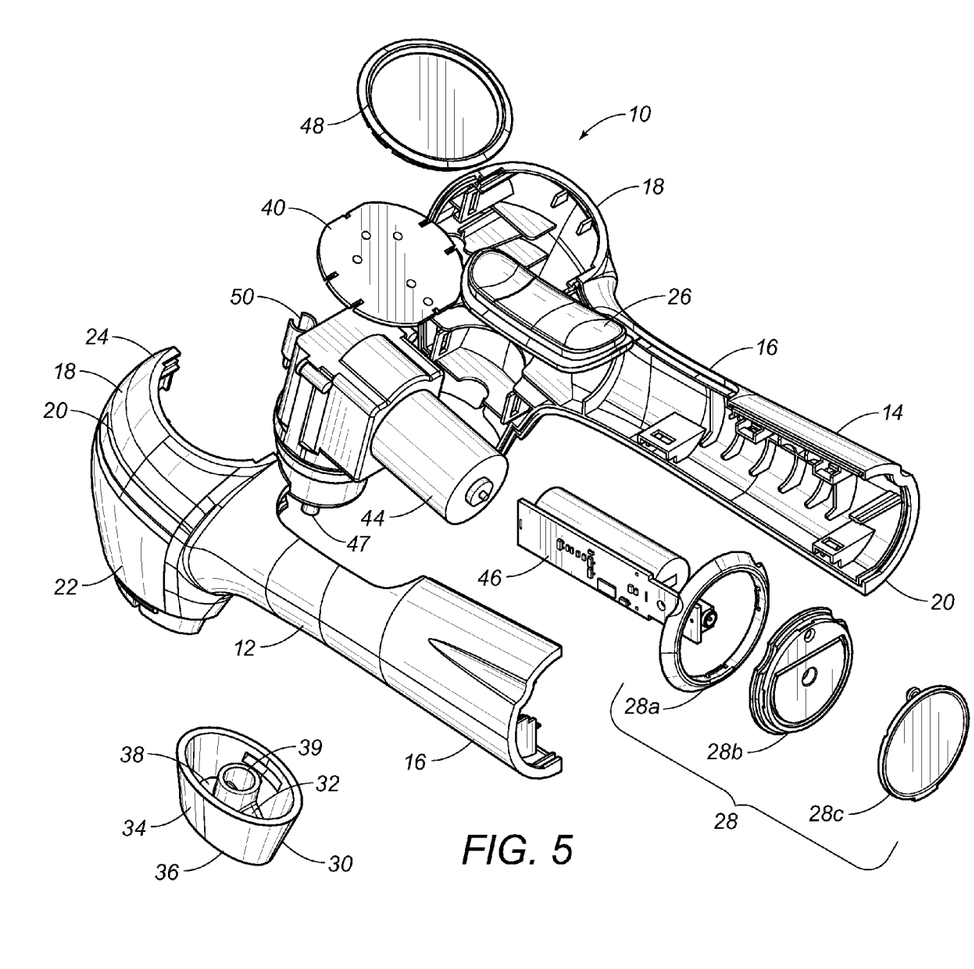
FIG. 5 is an exploded perspective view of an embodiment of the apparatus to administer a skin care composition, according to the present invention.

FIGS. 1-5 show embodiments of the housing 20 having a front side 12 and a back side 14. The housing 20 can be comprised of a handle portion 16 and a head portion 18. The head portion 18 is placed on top of the handle portion 16 and has a front end 22 and a back end 24. The front end 22 of the head portion 18 is the active end of the apparatus 10. The front end 22 is oriented toward the skin of the user. FIGS. 1-3 and 5 show the handle portion 16 with a grip means 26. The grip means 26 can be a tacky pad or surface to allow the apparatus 10 to be held with ease and comfort. The grip means 26 prevents slipping from the hand of the user so that the apparatus 10 maintains proper contact with the skin. FIGS. 1-3 and 5 show the grip means 26 facing the back side 14 of the housing 20. FIG. 1-5 show embodiments with a sealing cap 28 at an end of the handle portion 16, opposite the head portion 18. The sealing cap 28 encloses the components, including the control module 40, motor 42, suction pump 44, vibrator 50, and power supply 46, in the housing 20. FIG. 5 shows the sealing cap 28 comprised of a bezel 28a, end cap 28b, and rubber cap 28c.

Embodiments of the present invention include the suction tip 30 placed on the front end 22 of the head portion 18 so as to face the front side 12 of the housing 20. The suction tip 30 forms an area of negative pressure and interacts with skin of the user. As such, the suction tip 30 is made of material suitable for sealing contact with skin. The material can be pliable and flexible, such as polyethylene (PET). The material degrades from wear and requires replacement. The material can also be set to degrade at different rates for proper replacement and maintenance of the apparatus 10. The material must also resist irritating the skin, especially if sensitive skin of the user is being treated. Different materials may be used for softer skin and bony skin, depending on the user preferences. Different colors of materials can also be used to quickly identify the materials and types of suction tip 30 embodiments.

The suction tip 30 has variable shape and dimensions to seal against skin of different areas of the body. Parts of the body can be difficult to reach, and it can be more difficult to apply a skin care composition in difficult to reach areas. The suction tip 30 can be narrow or round, instead of wide and oval. A focused suction tip 30 can be narrow to concentrate on bony surfaces with less skin to grab. Additionally, the suction tip 30 can have different sizes to adapt to skin of different areas of the body. A larger suction tip 30 will more efficiently apply skin care composition to legs and thighs with a greater surface area than the cheeks and neck. The suction tip 30 can have various sizes to account for the different applications to the skin of different parts of the body. FIGS. 1-5 show a suction tip 30 that deforms inward toward the back end 24 of the head portion 18 so as to form the area of negative pressure on the skin. The area of negative pressure on the skin may become receptive to absorb the skin care composition on the skin.

FIGS. 1, 2, 4, 5 and 6 show an embodiment of the suction tip 30 comprising a suction cup 32, an outer wall 34, and a ridge 36. The suction cup 32 has a concave surface 38 facing outward to the front end 22 of the head portion 18. The outer wall 34 is in fixed engagement to the front end 22 of the head portion 18, and the ridge 36 is at a connection between the suction cup 32 and the outer wall 34. The ridge 36 forms a sealing engagement to skin and composition, framing the area of negative pressure. In some embodiments, the suction tip 30 is replaceable, such that the outer wall 34 separates from the head portion 18, so that a new suction tip 30 can be assembled. Any deterioration of the ridge 36 would prevent the seal and formation of the area of negative pressure. Replaceable suction tips 30 increase the working life of the apparatus 10. FIGS. 4 and 5 show an embodiment with a tubular receptacle 39 behind the concave surface 38. The tubular receptacle 39 engages the suction pump 44, so that the suction pump 44 can form the area of negative pressure. In some embodiments, there is a suction outlet 47, shown in FIG. 5. The suction outlet 47 extends from the suction pump 40 to direct suction force to through the suction tip 30.

Figure 7A:
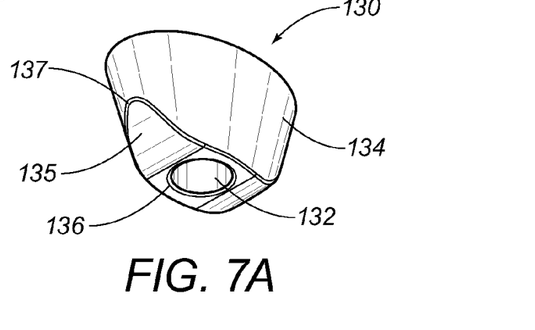
Figure 7B:
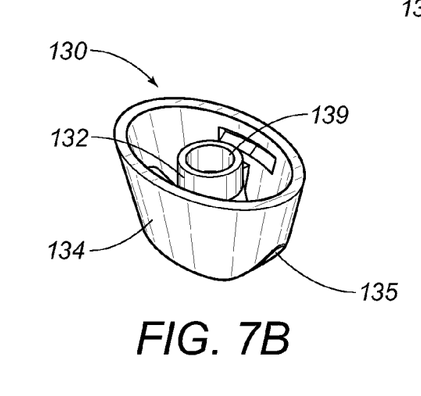

FIGS. 7A, 7B, 8A, and 8B also show alternative embodiments of the suction tip 130, 230. In FIGS. 7A and 7B, the suction tip 130 variation has a suction chamber 132, an outer wall 134, and a cover piece 137 connecting the outer wall 134 to the suction chamber 132. The cover piece 137 is made integral with the outer wall 134 and with the suction chamber 132 at a ridge 136. The cover piece 136 has a surface 135 oriented outward from the head portion 18. The area of negative pressure is still formed according to the ridge 136 placed on the skin surface. The ridge 136 is now defined by the cover piece 137 instead of the outer wall 134. There is more variability to have a surface 135 to glide over skin and smaller cross section. When the suction chamber 132 deforms inward toward the back end 24 of the head portion 18, the area of negative pressure is formed according to the ridge 136 on the cover piece 137. In FIGS. 7A and 7B, there can be a tubular receptacle 139 to engage the suction pump 44, so that the suction pump 44 can form the area of negative pressure. The suction outlet 47, as in FIG. 5, can extend from the suction pump 40 to direct suction force to through the suction tip 130.

Figure 8A:
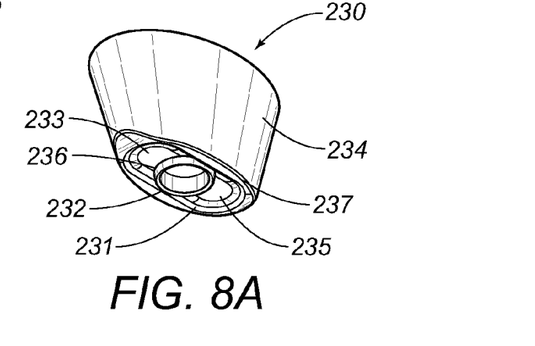
Figure 8B:
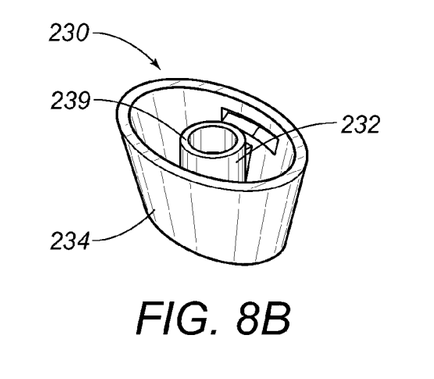

In FIGS. 8A and 8B, show a further embodiment of the suction tip 230 variation having a suction chamber 232, an outer wall 234, and a cover piece 237 connecting the outer wall 234 to the suction chamber 232. The cover piece 237 is similarly made integral with the outer wall 234 and with the suction chamber 232 at a ridge 236. This embodiment shows the cover piece 236 having a surface 235 oriented outward from the head portion 18 and having protrusions 231. The area of negative pressure is now formed according to the ridge 236 and protrusions 231 placed on the skin surface. The ridge 236 and protrusions 231 from a secondary suction chamber 233 in fluid connection with the suction chamber 232. The suction force is exerted by the suction chamber 232 and the secondary suction chamber 233 formed at the suction tip 232. The suction force can be split or oriented for a particular skin type. There are different zones of pressure. FIGS. 8A and 8B show a centralized suction force with some outer suction. There can also be a tubular receptacle 239 to engage the suction pump 44, so that the suction pump 44 can form the area of negative pressure. The suction outlet 47, as in FIG. 5, can extend from the suction pump 40 to direct suction force to through the suction tip 230.

The multiple embodiments of the suction tip 30, 130, 230 show variability to account for different areas of skin, which may require different attachments for the sealed relationship on the skin. Rougher skin and soft pliable skin have different properties, and embodiments of the suction tip 30, 130, 230 can account for these different properties. Other embodiments may include a flared outer wall for a trumpet shape. A flared version may cover a larger area of skin. There can be a mesh surface on the cover piece also for gliding along the skin and suction through the perforations of the mesh surface. There can also be a split or polarized suction chamber, as in FIGS. 8A and 8B, so that the suction grabs skin from the ends of the suction tip, instead of the center. The present invention covers these versions of a sealed ridge on the skin surface for the area of negative pressure concurrent with regulated vibration.

The present invention further includes the components of the control module 40, motor 42, suction pump 44, power supply 46, and vibrator 50 in the housing 20. The control module 40 is placed on the back end 24 of the head portion 18 with an interface 48 aligned with the handle portion 16 and facing the back side 14 of the housing 20 in embodiments of FIGS. 1, 3 and 5. FIG. 5 further shows the embodiment with the motor 42 contained in the head portion 18 of the housing 20 and connected to the control module 40. The suction pump 44 is contained in the front end 22 of the head portion 18 and connects to the motor 42. The power supply 46 is at least partially housed in the handle portion 16 and connects to the control module 40, the motor 42, and the vibrator 50. The vibrator 50 is mounted in the head portion 18 and also connects to the control module 40. The vibrator 50 generates vibrations to the suction tip 30. The control module 40 can be comprised of a printed circuit board (PCB) for regulating the motor 42, suction pump 44, power supply 46, and vibrator 50 at activity and intensity set by the user through the interface 48.

Figure 6:
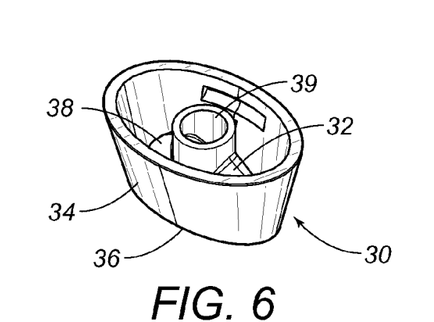
FIGS. 6, 7A, 7B, 8A, and 8B are perspective views of alternate embodiments of the suction tip of the present invention.

In the embodiment of FIGS. 4-6 with the tubular receptacle 39, the suction pump 44 can have a suction outlet 47 extending outward toward the suction tip 30. The suction outlet 47 engages the suction tip 30 to actuate the concave surface 38, which forms the area of negative pressure. In some embodiments, the suction outlet 47 inserts into the tubular receptacle 39. Exerting suction force through the suction outlet 47 by the suction pump 44 deforms the suction cup 32 inward toward the back end 24 of the head portion 18 so as to form the area of negative pressure. FIGS. 7A, 7B, 8A, and 8B show embodiments for the tubular receptacles 139, 239 engaging the suction outlet 47 for respective suction chambers 132, 232.

FIG. 5 shows the vibrator 50 as a vibrating means. Mechanical vibrations are generated and transmitted to the suction tip 30. In some embodiments, the vibrator 50 is fixedly attached to the suction pump 44, such that vibration of the suction pump 44 transmits vibration to the suction tip 30 at the ridge 36. The area of negative pressure is vibrated concurrent with the suction. In some embodiments, the vibrator 50 can be comprised of a magnet, a vibration motor, a weight, and a brush and commutator assembly. Movement of the weight within the head portion 18 generates the vibrations to the suction tip 30 and skin. FIG. 5 shows the vibrator 50 attached to a top of the suction pump 44 to set the vibrations. The mechanical movements of the vibrator 50 are transmitted from the vibrator 50 to the suction pump 44 and to the housing 20. The outer walls 34 of the suction tip 30 engage the housing 20 such that vibration of the housing 20 is transmitted to the suction tip 30. The engagement of the outer walls 34 on the housing 20 sets the vibrations, which do not dislodge or rupture the seal of the area of negative pressure. The amount of vibration is regulated by the control module 40 for consistent and controlled vibration force that can remain concurrent with the suction force. In some embodiments, the area of negative pressure is formed by the suction tip 30 before vibrations from the vibrator 50. The suction tip 30 can maintain the area of negative pressure concurrent with vibrations from the vibrator 50. As such, the suction force of the suction tip 30 can be greater than vibration force of the vibrator 50. The relationship of the vibrator 50 as a vibration means and suction pump 44 are coordinated to maintain the area of negative pressure during transmission of vibrations through the suction tip 30. Even with personalized settings for the intensity of the vibration, the apparatus 10 restricts the intensity of the vibration relative to the selected amount of suction force.

In some embodiments, there can also be a heating element, such as a laser. The heating element is mounted in the housing 20 to radiate heat to the area of negative pressure through the tubular receptacle 39 of the suction tip 30. The heat warms the skin to further enhance absorption of a skin care composition. The heating element is not shown in the drawings, but may be incorporated in connection to the control module 40 and the suction tip 30.

The method for administering a skin care composition with the apparatus 10 includes applying a skin care composition on a surface of skin. The skin care composition forms a layer of composition on any part of the body for treatment. The skin care composition may be quick or slow to evaporate as a baseline, and the method may increase the rate of absorption more than any other prior art device. The skin may be more apt to receive the composition. The composition may be more broken down for the skin. Next, the suction tip 30 is positioned in contact with the surface of skin and the layer of composition. A seal is formed with the suction tip 30 around the surface of skin. The control module 40 can activate the suction pump 44 to form the area of negative pressure on the surface of skin. The suction tip 30 defines the area of negative pressure within the suction tip 30, such as along the ridge 36 of the embodiment of FIG. 5.

Once the area of negative pressure is set, according to a setting of the control module 40, the method includes vibrating the area of negative pressure of the surface of skin with the vibrator 50. The control module 40 further regulates the intensity of vibration. The skin care composition may now be absorbed through the surface of skin at a rate affected by the area of negative pressure and mechanical vibration. The present invention may increase the rate of absorption. In some embodiments of the method, the step of vibrating of the area of negative pressure of the surface of skin is stopped, and the area of negative pressure of the surface of skin is released. Next, the steps are repeated as a pulsing effect of suction and suction with vibration. The forming of the area of negative pressure and vibrating the area of negative pressure can be repeated so as to be alternating between suction and suction with vibration. Further steps can include releasing the seal with the suction tip 30, and removing the suction tip 30 from the surface of skin. Excess skin care composition can now be removed from the surface of skin. The vibration remains concurrent with maintaining the area of negative pressure. In particular embodiments, the step of vibrating is concurrent with the suction cup 32 being actuated and the area of negative pressure being held constant, as in FIGS. 4-6.

Unlike prior art devices with only mechanical massaging or vacuum suction, the present invention incorporates a negative pressure and a particular type of mechanical massaging. In embodiments of the invention, the mechanical massaging is vibration. In addition to prior art suction force on the skin, the apparatus and method for administering a skin care composition includes a suction force with vibration force. There is a particular sequence of the established area of negative pressure and subsequent vibration. The strength of the vibration is further regulated to adjust to the strength of the seal of the area of negative pressure. The vibration cannot rupture the seal. The present invention further regulates and sets the vibration force to avoid interfering with the suction force, such that the particular interrelationship of the vibrator and suction tip are not disclosed in any prior art system. The vibration force can be concurrent and alternating, during an application of a suction force. The suction force should also be maintained concurrent with a vibration force. The apparatus and method for administering a skin care composition may affect the rate of absorption. The skin may be primed for increased receptivity. The composition may be broken down for more absorption. Administering the skin care composition with the area of negative pressure and vibration of the present invention has beneficial effects for the user.

The present invention further discloses the apparatus and method for administering a skin care composition tailored for preferences of an individual user. The control module can adjust the strength of the suction by the suction tip to form the area of negative pressure, while regulating vibrations from the vibrator to be prevent release of the seal on the area of negative pressure. The vibrator and suction pump are further related to have mechanical vibrations to maintain the area of negative pressure concurrent with the vibration. The amount of vibration can be controlled by the individual user and restricted to prevent releasing the seal. The seal can also be adjusted to be stronger to allow for stronger vibrations. There can be personalized settings for the amount and intensity of the suction and vibration, but the present invention still restricts those settings so as to maintain the area of negative pressure. Not just any amount of combining suction force and vibration force are proper for the present invention.

The foregoing disclosure and description of the invention is illustrative and explanatory thereof. Various changes in the details of the described system and method can be made without departing from the true spirit of the invention.

I claim:

1. An apparatus to administer a skin care composition, said apparatus comprising:
   a housing having a front side and a back side, said housing being comprised of a handle portion and a head portion, said head portion being placed on top of said handle portion, said head portion having a front end and a back end;
   a suction tip placed on said front end of said head portion so as to face said front side of said housing, said suction tip forming an area of negative pressure;
   a control module placed on said back end of said head portion with an interface aligned with said handle portion and facing a back side of said housing;
   a motor contained in said head portion of said housing and connected to said control module;
   a suction pump contained in said front end of said head portion of said housing, said suction pump being connected to said motor, said suction pump being controlled by said control module through said motor;
   a vibrator mounted in said head portion and connected to said control module, said vibrator generating vibrations to said suction tip; and
   a power supply, being at least partially housed in said handle portion and connected to said control module, said motor, and said vibrator,
   wherein said vibrator fixedly attaches to said suction pump, wherein said vibrator engages said suction pump so as to transmit vibrations through said head portion to said suction tip.

2. The apparatus to administer the skin care composition, according to claim 1, wherein said handle portion comprises a grip means, said grip means facing said back side of said housing.

3. The apparatus to administer the skin care composition, according to claim 1, wherein said housing further comprises a sealing cap at an end of said handle portion, opposite said head portion.

4. The apparatus to administer the skin care composition, according to claim 1, wherein said suction tip is comprised of a material suitable for sealing contact with different areas of skin.

5. The apparatus to administer the skin care composition, according to claim 1, wherein said suction tip comprises:
   a suction cup, having a concave surface facing outward to said front end of said head portion;
   an outer wall in fixed engagement to said front end of said head portion; and
   a ridge at a connection between said suction cup and said outer wall.

6. The apparatus to administer the skin care composition, according to claim 1, wherein said vibrator is comprised of a magnet, a vibration motor, a weight, and a brush and commutator assembly, said vibrator generating said vibrations by movement of said weight within said head portion.

7. The apparatus to administer the skin care composition, according to claim 1, wherein said suction tip maintains said area of negative pressure concurrent with vibrations from said vibrator.

8. The apparatus to administer the skin care composition, according to claim 1, wherein suction force of said suction tip is greater than vibration force of said vibrator.

9. An apparatus to administer the skin care composition, said apparatus comprising:
a housing having a front side and a back side, said housing being comprised of a handle portion and a head portion, said head portion being placed on top of said handle portion, said head portion having a front end and a back end;
a suction tip placed on said front end of said head portion so as to face said front side of said housing, said suction tip forming an area of negative pressure;
a control module placed on said back end of said head portion with an interface aligned with said handle portion and facing a back side of said housing;
a motor contained in said head portion of said housing and connected to said control module;
a suction pump contained in said front end of said head portion of said housing, said suction pump being connected to said motor, said suction pump being controlled by said control module through said motor;
a vibrator mounted in said head portion and connected to said control module, said vibrator generating vibrations to said suction tip; and
a power supply, being at least partially housed in said handle portion and connected to said control module, said motor, and said vibrator,
wherein said suction tip comprises:
a suction cup, having a concave surface facing outward to said front end of said head portion;
an outer wall in fixed engagement to said front end of said head portion; and
a ridge at a connection between said suction cup and said outer wall, and
wherein said suction cup is comprised of a tubular receptacle behind said concave surface.

10. The apparatus to administer the skin care composition, according to claim 9, wherein said suction pump comprises a suction outlet extending outward toward said suction tip, said suction outlet being inserted into said tubular receptacle.

11. An apparatus to administer the skin care composition, said apparatus comprising:
a housing having a front side and a back side, said housing being comprised of a handle portion and a head portion, said head portion being placed on top of said handle portion, said head portion having a front end and a back end;
a suction tip placed on said front end of said head portion so as to face said front side of said housing, said suction tip forming an area of negative pressure;
a control module placed on said back end of said head portion with an interface aligned with said handle portion and facing a back side of said housing;
a motor contained in said head portion of said housing and connected to said control module;
a suction pump contained in said front end of said head portion of said housing, said suction pump being connected to said motor, said suction pump being controlled by said control module through said motor;
a vibrator mounted in said head portion and connected to said control module, said vibrator generating vibrations to said suction tip; and
a power supply, being at least partially housed in said handle portion and connected to said control module, said motor, and said vibrator,
wherein said suction tip comprises:
a suction chamber, having a generally concave surface facing outward to said front end of said head portion;
an outer wall in fixed engagement to said front end of said head portion; and
a cover piece connecting said outer wall to said suction chamber, said cover piece being made integral with said outer wall and having a surface oriented outward from said head portion, said cover piece being made integral with said suction chamber at a ridge,
wherein said area of negative pressure is formed according to said ridge.

12. The apparatus to administer the skin care composition, according to claim 11, wherein said suction chamber is comprised of a tubular receptacle behind said concave surface, and wherein said suction pump comprises a suction outlet extending outward toward said suction tip, said suction outlet being inserted into said tubular receptacle.

13. The apparatus to administer the skin care composition, according to claim 11, wherein said surface oriented outward from said head portion is comprised of protrusions, said protrusions forming secondary suction chambers in fluid connection with said suction chamber.

14. A method for administering a skin care composition, said method comprising the steps of:
applying a skin care composition on a surface of skin, said skin care composition forming a layer of composition;
positioning said suction tip of said apparatus, according to claim 1, in contact with said surface of skin and said layer of composition;
forming a seal with said suction tip around said surface of skin;
forming an area of negative pressure on said surface of skin by activating said suction pump;
vibrating said area of negative pressure of said surface of skin with said vibrator;
ceasing the step of vibrating of said area of negative pressure of said surface of skin;
releasing said area of negative pressure of said surface of skin, after said step of ceasing the step of vibrating; and
warming said area of negative pressure.

15. The method for administering the skin care composition, according to claim 14, further comprising the steps of:
releasing said seal with said suction tip; and
removing said suction tip from said surface of skin.

16. The method for administering the skin care composition, according to claim 15, further comprising the step of removing excess skin care composition from said surface of skin.

17. The method for administering the skin care composition, according to claim 14, further comprising the step of:
repeating the steps of forming said area of negative pressure with said suction pump, vibrating said area of negative pressure with said vibrator, ceasing the step of vibrating, and releasing said area of negative pressure of said surface of skin,
wherein the step of repeating the steps comprised pulsing said area of negative pressure of said surface of skin with vibration and suction.

18. The method for administering the skin care composition, according to claim 14, wherein said step of vibrating comprises regulating intensity of vibration to maintain said area of negative pressure.

* * * * *